(12) United States Patent
Salters

(10) Patent No.: US 11,090,401 B2
(45) Date of Patent: Aug. 17, 2021

(54) SAFETY IMPROVEMENT FOR UV APPLICATIONS BY MONITORING CHANGES IN UV OUTCOUPLING

(71) Applicant: KONINKLIJKE PHILIPS N.V., Eindhoven (NL)

(72) Inventor: Bart Andre Salters, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 81 days.

(21) Appl. No.: 16/610,631

(22) PCT Filed: May 17, 2018

(86) PCT No.: PCT/EP2018/062829
§ 371 (c)(1),
(2) Date: Nov. 4, 2019

(87) PCT Pub. No.: WO2018/215272
PCT Pub. Date: Nov. 29, 2018

(65) Prior Publication Data
US 2021/0154344 A1 May 27, 2021

(30) Foreign Application Priority Data

May 23, 2017 (EP) .................................. 17172508.8

(51) Int. Cl.
*A61L 2/24* (2006.01)
*A61L 2/10* (2006.01)
(Continued)

(52) U.S. Cl.
CPC .................... *A61L 2/24* (2013.01); *A61L 2/10* (2013.01); *B08B 7/0057* (2013.01); *B08B 13/00* (2013.01);
(Continued)

(58) Field of Classification Search
CPC .......... A61L 2/24; A61L 2/10; A61L 2202/11; A61L 2202/14; A61L 2202/24;
(Continued)

(56) References Cited

U.S. PATENT DOCUMENTS 6,277,330 B1 * 8/2001 Liu ...................... G01N 21/552
422/82.05
9,611,018 B2 4/2017 Salters et al.
(Continued)

FOREIGN PATENT DOCUMENTS

CN 201450649 U 5/2010
DE 102008063887 A1 7/2010

OTHER PUBLICATIONS

Search Report and Written Opinion from PCT/EP2018/062829 dated Aug. 27, 2018.

*Primary Examiner* — Nicole M Ippolito

(57) ABSTRACT

The invention provides an system (200) comprising (i) a light source (220) configured to provide radiation (221), wherein the radiation (221) at least comprises UV radiation; (ii) a waveguide element (1210) comprising a radiation exit window (230), wherein the waveguide element (1210) is configured to receive at least part of the radiation (221) and to radiate at least part of the radiation (221) to the exterior of the waveguide element (1210) via the radiation exit window (230) and configured to internally reflect part of the radiation (221) at the radiation exit window (230); (iii) an optical sensor (310) configured to sense an internal reflection intensity (I) of the internally reflected radiation (221); and (iv) a control system (300), functionally coupled to the optical sensor, and configured to reduce the intensity of the radiation (221) as function of reaching a predetermined first threshold of a reduction of the internal reflection intensity (I) over a time.

17 Claims, 6 Drawing Sheets

(51) Int. Cl.
  *B08B 7/00* (2006.01)
  *B08B 17/02* (2006.01)
  *B08B 13/00* (2006.01)
  *B63B 59/04* (2006.01)
  *E05B 1/00* (2006.01)
  *G02B 6/42* (2006.01)
(52) U.S. Cl.
  CPC ............ *B08B 17/02* (2013.01); *G02B 6/4286* (2013.01); *A61L 2202/11* (2013.01); *A61L 2202/14* (2013.01); *A61L 2202/24* (2013.01); *A61L 2202/25* (2013.01); *B63B 59/04* (2013.01); *E05B 1/0069* (2013.01)
(58) Field of Classification Search
  CPC ... A61L 2202/25; B63B 59/04; E05B 1/0069; B08B 7/0057; B08B 13/00; B08B 17/02; G02B 17/02
  USPC ... 250/453.11, 454.11, 455.11, 493.1, 494.1, 250/504 R
  See application file for complete search history.

(56) References Cited

U.S. PATENT DOCUMENTS

| | | | |
|---|---|---|---|
| 10,252,783 | B2 | 4/2019 | Salters et al. |
| 2002/0013425 | A1* | 1/2002 | Johnson .................. C08L 63/00 525/438 |
| 2008/0095661 | A1 | 4/2008 | Kohler |
| 2009/0110356 | A1* | 4/2009 | Xiang ...................... G02B 6/10 385/129 |
| 2011/0291995 | A1 | 12/2011 | Shr et al. |
| 2014/0131595 | A1 | 5/2014 | Nathan et al. |
| 2016/0002580 | A1* | 1/2016 | Erickson ................ C12M 29/16 435/134 |
| 2017/0115235 | A1 | 4/2017 | Ohlsson et al. |
| 2017/0197693 | A1 | 7/2017 | Salters et al. |

\* cited by examiner

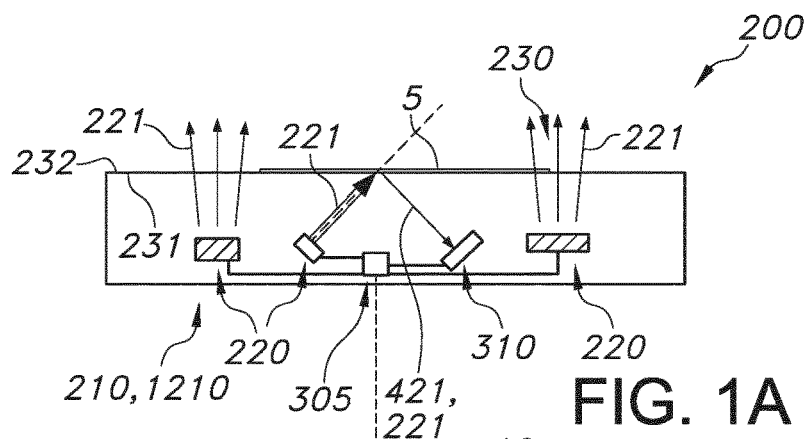
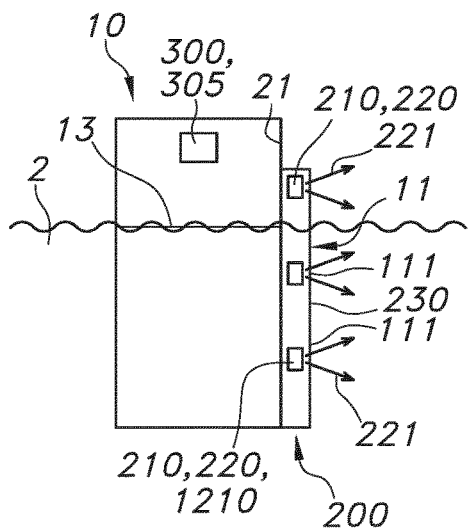
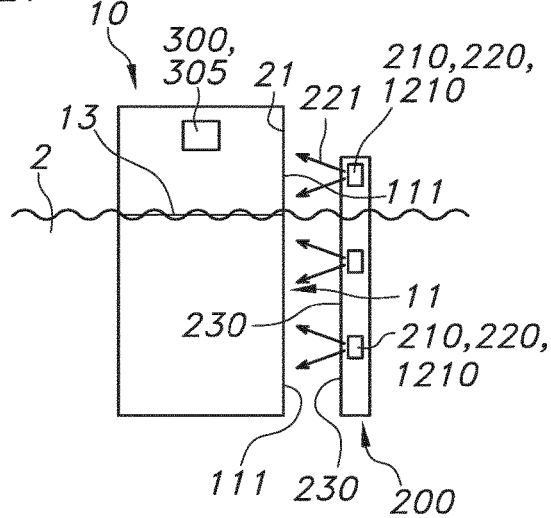
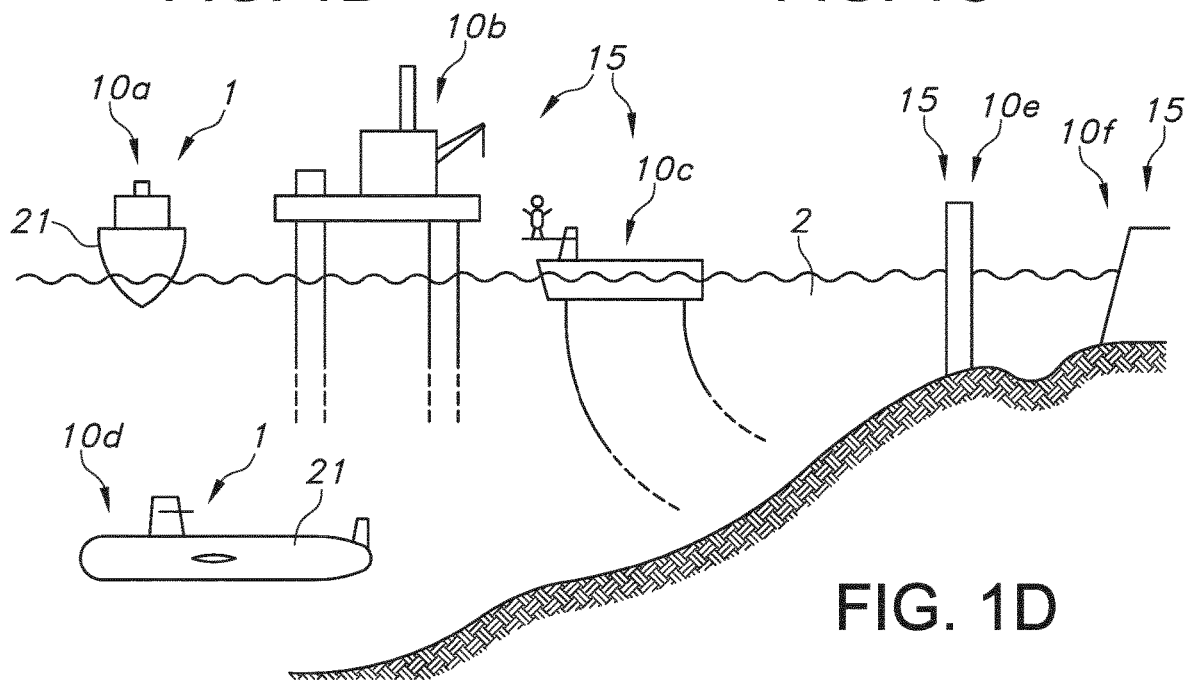

SAFETY IMPROVEMENT FOR UV APPLICATIONS BY MONITORING CHANGES IN UV OUTCOUPLING

CROSS-REFERENCE TO PRIOR APPLICATIONS

This application is the U.S. National Phase application under 35 U.S.C. § 371 of International Application No. PCT/EP2018/062829, filed on May 17, 2018, which claims the benefit of EP Patent Application No. EP 17172508.8, filed on May 23, 2017. These applications are hereby incorporated by reference herein.

FIELD OF THE INVENTION

The invention relates to an (anti-biofouling) system. The invention also relates to an object which includes such (anti-biofouling) system. The invention also provides a method for controlling escape of UV radiation from a waveguide (of such (anti-biofouling) system)). Further, the invention relates to a method for providing such waveguide or (anti-biofouling) system to an object.

BACKGROUND OF THE INVENTION

Anti-biofouling methods are known in the art. WO 2016192942 A1 (Koninklijke Philips N.V.), for instance, describes an object that during use is at least partly submerged in water, the object further comprising an anti-biofouling system comprising an UV emitting element for application of UV radiation, wherein the UV emitting element especially comprises one or more light sources, even more especially one or more solid state light sources, and is configured to irradiate with said UV radiation (during an irradiation stage) one or more of (i) a (said) part of said external surface and (ii) water adjacent to said part of said external surface, wherein the object is especially selected from the group consisting of a vessel and an infrastructural object.

Especially, the object, or the anti-biofouling system, comprise(s) a control system. Hence, the object comprises such comprises such control system, which may optionally be integrated in the anti-biofouling system, or elsewhere in the object.

In a specific embodiment, the control system is especially configured to control said UV radiation as function of input information comprising information of one or more of (i) a location of the object, (ii) movement of the object, (iii) a distance (d) of (said part of) the object to a second object, and (iv) a position of the part of the external surface relative to the water. Hence, especially the anti-biofouling system is configured to control said UV radiation as function of input information comprising information of a human UV radiation exposure risk.

SUMMARY OF THE INVENTION

Biofouling or biological fouling (herein also indicated as "fouling" or "biofouling") is the accumulation of microorganisms, plants, algae, and/or animals on surfaces. The variety among biofouling organisms is highly diverse and extends far beyond attachment of barnacles and seaweeds. According to some estimates, over 1700 species comprising over 4000 organisms are responsible for biofouling. Biofouling is divided into microfouling which includes biofilm formation and bacterial adhesion, and macrofouling which is the attachment of larger organisms. Due to the distinct chemistry and biology that determine what prevents organisms from settling, these organisms are also classified as hard or soft fouling types. Calcareous (hard) fouling organisms include barnacles, encrusting bryozoans, mollusks, polychaete and other tube worms, and zebra mussels. Examples of non-calcareous (soft) fouling organisms are seaweed, hydroids, algae and biofilm "slime". Together, these organisms form a fouling community. Herein, "biofouling" may in embodiments also related to bacteria.

In several circumstances biofouling creates substantial problems. Machinery stops working, water inlets get clogged, and hulls of ships suffer from increased drag. Hence the topic of anti-fouling, i.e. the process of removing or preventing fouling from forming, is well known. In industrial processes, bio-dispersants can be used to control biofouling. In less controlled environments, organisms are killed or repelled with coatings using biocides, thermal treatments or pulses of energy. Non-toxic mechanical strategies that prevent organisms from attaching include choosing a material or coating with a slippery surface, or creation of nanoscale surface topologies similar to the skin of sharks and dolphins which only offer poor anchor points. Biofouling on the hull of ships causes a severe increase in drag, and thus increased fuel consumption. It is estimated that an increase of up to 40% in fuel consumption can be attributed to biofouling. As large oil tankers or container transport ships can consume up to €200.000 a day in fuel, substantial savings are possible with an effective method of anti-biofouling.

It surprisingly appears that one may effectively use UV radiation to substantially prevent biofouling on surfaces that are in contact with sea water or water in lakes, rivers, canals, etc. Herewith, an approach is presented based on optical methods, in particular using ultra-violet light or radiation (UV). It appears that most micro-organisms are killed, rendered inactive or unable to reproduce with sufficient UV light. This effect is mainly governed by the total dose of UV light. A typical dose to kill 90% of a certain micro-organism is 10 mW/h/m$^2$.

UV LEDs or UV sources may operate with limited wall plug efficiency and limited lifetime. This may limit the use of such light sources.

UV radiation, however, can also be used for applications other than anti-fouling of aquatic (such as marine) objects. UV radiation may also be used to clean objects or to keep objects clean from bacteria, etc.

The term "aquatic" and similar terms may refer to both freshwater and salt water applications (and of course also brackish water applications).

In all such examples, it may be necessary to take specific measures when higher organisms, including humans, may receive such UV radiation, especially when it is possible to physically contact radiation emitting surfaces.

Hence, it is an aspect of the invention to provide an alternative system or method for prevention or reduction of biofouling, which preferably further at least partly obviates one or more of above-described drawbacks. The present invention may have as object to overcome or ameliorate at least one of the disadvantages of the prior art, or to provide a useful alternative.

As the system may be used to neutralize bacteria and/or other microorganisms, or to prevent attachment of bacteria and/or microorganisms, the anti-biofouling system may in general also be indicated as "system" and in specific embodiments "anti-micro biological fouling system", or "hygiene system", etcetera. Herein, the system may further be indicated as "anti-biofouling system" or "system".

Herein, a new approach based on optical means is proposed. Amongst others, this new approach may be based on the following aspects:

Light is coupled out of the surface, if 'something' touches the surface. This outcoupling means that less light will stay inside the light guide. This can be monitored.

Fouling will couple out light, just as well as higher organisms and objects; for instance a human hand touching the surface;

Fouling will gradually cover a surface; where a hand touching the surface causes a very sudden, immediate change in the outcoupling.

Hence, especially it is herein proposed to monitor over time the total amount of light that stays within the light guide, by means of an integrated UV sensor. If the change in the amount of outcoupled light is slow (the first derivative of the signal is small), this implies that fouling is occurring, all over the surface at a gradual pace. However, if a large step if observed in this signal (large first derivative), a large object has touched the surface. This cannot be fouling, and thus it has to be assumed something else—like a human being—has touched the surface. As this implies extra light is coupled out, and it simultaneously implies that a human being is near, the decision has to be made to shut off the light; at least temporarily.

In an aspect, the invention provides an anti-biofouling system ("system" or "anti-fouling system" or "lighting system") comprising: (i) a waveguide element (or "waveguide" or "light guide") comprising a radiation exit window; (ii) an optical sensor ("sensor") configured to sense an internal reflection intensity (I) of internally reflected radiation; (iii) a control system, functionally coupled to the optical sensor. Especially, the waveguide element is configured to receive radiation (from a light source), wherein the radiation at least comprises UV radiation, and configured to radiate at least part of the radiation to the exterior of the waveguide element via the radiation exit window and configured to internally reflect part of the radiation at the radiation exit window. Further, the control system may especially be configured to reduce the intensity of the radiation as function of reaching a predetermined first threshold of a reduction of the internal reflection intensity (I) over time. Therefore, the invention especially provides an anti-biofouling system comprising: (i) a waveguide element comprising a radiation exit window, wherein the waveguide element is (a) configured to receive radiation (from a light source), wherein the radiation at least comprises UV radiation, and (b) configured to radiate at least part of the radiation to the exterior of the waveguide element via the radiation exit window, and (c) configured to internally reflect part of the radiation at the radiation exit window; (ii) an optical sensor ("sensor") configured to sense an internal reflection intensity (I) of the internally reflected radiation; (iii) a control system, functionally coupled to the optical sensor, and configured to reduce the intensity of the radiation as function of reaching a predetermined first threshold of a reduction of the internal reflection intensity (I) over time. Especially, such system(s) may further comprise a light source configured to provide radiation, wherein the radiation at least comprises UV radiation.

In a further aspect, the invention provides an anti-biofouling system comprising: (i) a light source configured to provide radiation, wherein the radiation at least comprises UV radiation; (ii) a waveguide element comprising a radiation exit window, wherein the waveguide element is configured to receive at least part of the radiation and to radiate at least part of the radiation to the exterior of the waveguide element via the radiation exit window and configured to internally reflect part of the radiation at the radiation exit window; (iii) an optical sensor configured to sense an internal reflection intensity (I) of the internally reflected radiation; and (iv) a control system, functionally coupled to the optical sensor. The control system may be configured to decrease the intensity of the radiation (especially the UV radiation) when the intensity of the internal reflection, as sensed by the sensor, reduces (by a sudden step). Therefore, in specific embodiments, the control system may be configured to reduce the intensity of the radiation as function of reaching a predetermined first threshold of a reduction of the internal reflection intensity (I) over time.

In yet a further aspect, the invention also provides an object that in embodiments during use is at least partly submerged in water, the object comprising the anti-biofouling system as defined herein, wherein the waveguide element is configured to irradiate with radiation during an irradiation stage one or more of (i) a part of an external surface of said object and (ii) water adjacent to said part of said external surface. In embodiments, the object may be selected from the group consisting of a vessel and an infrastructural object. In yet a further aspect, the invention provides an object comprising the anti-biofouling system as defined herein, wherein the object comprises an external surface, and wherein the radiation exit window is configured as at least part of the external surface, such as wherein the object is selected from the group comprising a door knob, a tap knob, a toilet knob, a railing, a kitchen cutting board, and a medical device, or (other) common household objects (that especially can be used at home or in offices, etc.), etcetera (for instance, some other examples are elsewhere described herein). The invention is further especially explained with reference to the anti-biofouling system in combination with the object.

With the present anti-biofouling system it may be possible to execute in a safer way the anti-fouling. When a hand touches the surface of the waveguide or when e.g. a dolphin touches the surface of the waveguide at a ship hull, the system may reduce or switch off the UV radiation. Especially, the system may switch off or reduce the UV radiation at the place where the higher organism touches the waveguide. Of course, the UV radiation can be increased again or switched on when the higher organism is removed from the waveguide. Due to contact with the waveguide, more radiation may be outcoupled, which leads to a reduction in the internal reflection; this effect may be described in terms of frustrated (total) internal reflection. Hence, the sensor senses (in an indirect way) the presence of an element on the window. Of course, buildup of fouling may lead to a gradual decrease of the internal reflection (assuming that the biofouling is not removed by the anti-fouling radiation). However, this will be a gradual build up, whereas contact with a higher organism will in general be sudden. When such contact is detected due to a sudden leakage of radiation, then the UV radiation intensity may be reduced for safety reasons. Reducing the intensity may include switching off, switching off locally, reducing the intensity (but not reducing to zero), or locally reducing the intensity (but locally not reducing to zero).

Instead of the term "waveguide element" also the term UV-emitting element may be used. Especially, the waveguide element is configured to provide, during use of the system, UV radiation.

Especially, in embodiments it may be that the control system takes into account a short delay before changing the UV intensity as the contact may be very temporary, and the amount of internal reflection will quickly return to the former level. In such instance, it may not be necessary to reduce the UV intensity. Therefore, in embodiments the control system is configured to reduce the intensity of the radiation only when in a predetermined control period a predetermined second threshold of an increase of the internal reflection intensity (I) (over time) does not occur. Especially, the control system will only change the intensity of the radiation when the reduced internal reflection intensity lasts for at least 0.1 seconds, such as at least 0.5 seconds, such as at least 1 second. Then, it is clear that it is not an occasional contact. However, when the internal reflection suddenly decreases, but within a (short) predetermined time increases again (to essentially the original level), this may be an occasional contact and the UV intensity is not necessarily reduced. Nevertheless, for safety reasons in embodiments any (quick) reduction of the internal reflection may (immediately) may be followed by a reduction of the UV intensity.

For instance, assuming a door knob comprising radiation transmissive material wherein with UV radiation the knob is kept clean, when touching (the transmissive material of) the door knob with the hand, the UV radiation may be switched off. After losing grip, the intensity can be increased again.

The control system may be configured such that when a essentially black element is brought into contact with the waveguide, the control system reduces the UV intensity. This element may e.g. be in physical contact with 10 cm$^2$ of the waveguide, such as only 4 cm$^2$ of the waveguide, like only 1 cm$^2$ of the waveguide. This kind of reference shows how the control system may be configured to safely operate the system. Therefore, in specific embodiments the predetermined first threshold is defined such that it would at least be reached when an object is brought into contact with the radiation exit window and covers 1 cm$^2$ of the radiation exit window, wherein the part of the object in contact with the radiation exit window is absorbing at least 90% of the radiation that is coupled out from the radiation exit window.

For instance, in specific embodiments the predetermined first threshold of a reduction of the internal reflection intensity (I) over time is a reduction of the internal reflection intensity (I) sensed by the optical sensor of at least 1%, such as at least 2%, like at least 5%, such as at least 10%, such as at least 15%, like at least 20%, in (a time period of) at maximum 0.05 seconds, such as in at maximum 0.1 seconds, especially in at maximum 0.5 seconds, such as in at maximum 1 second, like in at maximum 2 seconds, such as in at maximum 5 seconds, such as at maximum 10 seconds. A reduction of the internal reflection intensity by at least n %, such as 10%, implies that relative to a starting level, the internal reflection drops with n %, such as 10%.

Herein, especially the term "threshold" refers to the level that must be reached (or passed) for an effect to be produced. Hence, when e.g. a first threshold of a reduction of at least 1% in at maximum 0.1 seconds is reached (or passed), such as by way of example 1% in 0.1 seconds (exact first threshold value), or 5% in 0.05 seconds (larger than the first threshold value (as the intensity is larger and the time is shorter)), the UV radiation will be reduced (by the control system). An example would be a reduction of 100 mW to 90 mW (see also example below) or of 50 mW to 45 mW, which are both a reduction of 10%.

When a threshold is reached or passed, the threshold is passed and the UV radiation can be reduced (when reaching the first threshold) or increased (when reaching the second threshold).

Hence, in specific embodiments the reduction in internal reflection intensity (I) sensed by the optical sensor, $\Delta I$, and the time period, $\Delta t$, in which such reduction should occur may lead to a first threshold selected from the range of $0.1\%/s \leq |\Delta I/\Delta t| \leq 100\%/s$ (wherein $\Delta I<0\%$). Herein, $\Delta I$ is defined as the final intensity minus the intensity at the beginning of the time period, both indicated in percentage, wherein the intensity at the beginning of the time period is by definition 100%. Just by way of example: assume a signal at t=0 of 100 mW and a signal of 90 mW at the end of the time period (after e.g. 0.5 seconds). Then, $\Delta I=-10\%$. Hence, a reduction in the sensor signal (i.e. a reduced internal reflection) by definition leads to a negative $\Delta I$. The example reduction of 10 mW reduction in 0.5 seconds, starting at 100 mW at 0 S would provide $|\Delta I/\Delta t|=|-10\%/0.5\ s|=20\%/s$, which is in the range for the choice of the first threshold. This might thus be a suitable choice for the first threshold.

Would a threshold be defined larger than the indicated range, the sensitivity may not be high enough.

Any reduction equal to or larger than such predetermined first threshold may lead to a reduction in the intensity of the UV radiation. Note that especially $\Delta t$ is at maximum 2 seconds, such as at maximum 1 second. Hence, would the first threshold be reached in e.g. more than 10 seconds, this might qualify as a gradual build-up of fouling, or, at least not a physical contact of higher organism, such as a human, with the radiation exit window. Hence, such reduction of the reflection would not be qualified as a sudden step. Hence, e.g. assuming a first threshold level determined at $|\Delta I/\Delta t|=50\%/s$, then, when this first threshold is reached (or passed), such as by way of example 50% in 1 seconds (exact first threshold value), or 80% in 0.5 seconds (larger than the first threshold value), the UV radiation will be reduced.

Therefore, in embodiments the predetermined first threshold is selected from the range of $0.1\%/s \leq |\Delta I/\Delta t| \leq 100\%/s$, wherein $\Delta I$ is the reduction in internal reflection intensity (I) in percent (sensed by the optical sensor), wherein $\Delta I<0\%$, wherein $\Delta t$ is the time period in which such reduction $\Delta I$ occurs, wherein $\Delta t$ is at maximum one of the above indicated time periods, such as at maximum 1 second. The Internal reflection intensity at t=0 is defined as 100%.

With such data, a derivate may be evaluated. This again can be used to evaluate whether or not it is a gradual fouling or a contact with another element, such as a higher organism.

As indicated above, when the higher organism leaves again the surface of the waveguide, such as after losing grip of a door knob, the intensity can be increased again. Therefore, in specific embodiments the control system is configured to increase the intensity of the radiation as function of a predetermined second threshold of an increase of the internal reflection intensity (I) over time.

Alternatively or additionally, as minimum decrease in internal reflection intensity I also a predetermined minimum sensor signal (drop) may be defined (by way of example −1 mV).

For the second threshold, essentially the same numbers as defined above can be used, taking into account that touching the surface may lead to a reduction in the sensed internal reflection, and removal of an object of the surface may lead to (again) an increase in the sensed internal reflection.

Likewise, therefore in specific embodiments in specific embodiments, the increase in internal reflection intensity (I) sensed by the optical sensor, $\Delta I$, and the time period $\Delta t$ in which such increase should occur may lead to a first threshold selected from the range of $0.1\%/s \leq |\Delta I/\Delta t| \leq 400\%/s$ (wherein $\Delta I>0\%$). As indicated above, herein $\Delta I$ is defined as the final intensity minus the intensity at the beginning of the time period, both indicated in percentage, wherein the intensity at the beginning of the time period is by definition 100%. Just by way of example: assume a signal at t=0 of 100 mW and a signal of 110 mW at the end of the time period (after e.g. 0.5 seconds). Then, ΔI=+10%. Hence, an increase in the sensor signal (i.e. an increased internal reflection) leads by definition to a positive ΔI.

Any increase equal to or larger than such predetermined first threshold may lead to an increase in the intensity of the UV radiation. Note that especially Δt is at maximum 2 seconds, such as at maximum 1 second. Hence, would the second threshold be reached in e.g. more than 10 seconds, this might qualify as a gradual removal of fouling, or, at least not a retreated of higher organism, such as a human, from the radiation exit window. Hence, such increase of the reflection would not be qualified as a sudden step. Hence, e.g. assuming a second threshold level determined at |ΔI/Δt|=50%/s, then, when this first threshold is reached (or passed), such as by way of example 50% in 1 seconds (exact second threshold value), or 80% in 0.5 seconds (larger than the second threshold value), the UV radiation may be increased (again) (to e.g. the earlier UV radiation intensity before the drop). The internal reflection intensity at t=0 is defined as 100% (unless the intensity is 0).

Hence, as minimum increase in internal reflection intensity I also a predetermined minimum sensor signal (increase) may be defined (by way of example 1 mV).

Therefore, in embodiments the predetermined second threshold is selected from the range of 0.1%/s≤|ΔI/Δt|≤400%/s, wherein ΔI is the increase in internal reflection intensity (I) in percent (sensed by the optical sensor), wherein ΔI>0%, wherein Δt is the time period in which such reduction ΔI occurs, wherein Δt is at maximum one of the above indicated time periods, such as at maximum 1 second. Note that a drop cannot be larger than 100%, whereas an increase can be larger than 100%.

Hence, especially the control system is configured to switch off the radiation as function of reaching the predetermined first threshold of the reduction of the internal reflection intensity (I) over time and to switch on the radiation as function of a predetermined second threshold of an increase of the internal reflection intensity (I) over time.

Hence, in such an embodiment the UV radiation of a (single) light source is entirely switched off (and on). However, it may also be possible to reduce the intensity, such as to a level of 50%, or lower. Therefore, in embodiments the control system is configured to reduce the radiation as function of reaching the predetermined first threshold of the reduction of the internal reflection intensity (I) over time to a first intensity level of the radiation larger than 0 W, and to increase the radiation as function of the predetermined second threshold of the increase of the internal reflection intensity (I) over time to a predetermined second intensity level of the radiation.

When the system is a "simple" on/off system, the system switches the light source on to its predetermined fixed level. However, it may also be possible that the intensity of the lights source is controllable. As further elucidated below, the intensity may e.g. be a function of the extent of fouling, which may thus be measured with the optical sensor. This may also apply that it is desirable when, after a reduction in intensity, the light source is again switched to its former level, before the reduction in intensity. Therefore, in specific embodiments the predetermined second intensity level of the radiation is the intensity level of the radiation before the (most recent) reduction (or "drop") to the first intensity level of the radiation +/−20%, such as +/−10%. Hence, in embodiments the predetermined second intensity level of the radiation is in the range of +/−10% of the intensity level of the radiation before the reduction to the first intensity level of the radiation.

Of course, it may also be possible that in the meantime the surface of the waveguide has further been biofouled, or fouling has been removed, such as due to spontaneous removal. Hence, a return to the original value may then be less desirable in such occasions. Hence, in embodiments the anti-biofouling system may be configured to radiate at least part of the radiation to the exterior of the waveguide element according to a predetermined relation between intensity of the radiation and the internal reflection intensity (I) sensed by the optical sensor. This allows a control of the UV radiation as function of the (indirectly) sensed biofouling. The biofouling is (indirectly) sensed by the optical sensor. Hence, in such embodiments, the predetermined second intensity level of the radiation is (simply) the intensity level of the radiation associated (according to the predetermined relation between intensity of the radiation and the internal reflection intensity (I) sensed by the optical sensor) with the internal reflection intensity (I) sensed by the optical sensor. To this end the control system may comprise a memory storing predetermined relation(s) between intensity of the radiation and the internal reflection intensity (I) sensed by the optical sensor.

For specific applications, where safety may be very important, it may be possible that an increase of the UV radiation may only be executed upon instruction of a human. Therefore, in specific embodiments the anti-biofouling system may comprise a user interface, wherein the control system further comprises a safety routine, such that after a reduction of the intensity of the radiation due to reaching the predetermined first threshold of the internal reflection intensity (I), the intensity of the radiation can only be increased upon an instruction via the user interface. Here, the first threshold may also refer to an intensity threshold.

Note that in yet further embodiments, any decrease above the predefined first threshold may lead to a reduction of the anti-biofouling radiation. For instance, such embodiments may be chosen for safety reasons.

As indicated above, the anti-biofouling system comprises a UV-emitting element. The term "UV-emitting element" may also refer to a plurality of UV-emitting elements. Hence, the system may include a plurality of such elements. The system may include a source of electrical energy, but the system may (during use) also be functionally coupled with a source of electrical energy. In embodiments, each UV-emitting element may functionally be coupled with a source of energy. This allows a decentral powering of the UV-emitting elements. The source of energy is especially used for powering the light source(s).

Herein, the UV-emitting element can also be indicated as "lighting module". The UV-emitting element may be a plate-like module (herein also indicated as "optical medium"), with one or more relevant elements at least partly, or even entirely, embedded therein. Hence, in embodiments the UV-emitting element comprises light transmissive (solid) material, such as silicone, etc. However, the UV element may also include a housing enclosing at least partly, or even entirely, one or more relevant elements. The one or more relevant elements at least comprise the light source, which is configured to provide light source light, especially the UV radiation. The UV-emitting element may have a flat or a curved radiation exit window. The term "UV-emitting element" indicates that the element is especially configured to provide UV radiation during use of the element.

The waveguide element may be shaped as a plate, optionally a curved shape. However, the waveguide element may also have other shapes. This may depend e.g. from the application. For instance, when the object is a door knob, a tap knob, a toilet knob, a railing, a kitchen cutting board, or a medical device, the shape of the waveguide element may be or need to be different than a plate, and may have one or more curved faces.

The UV-emitting element comprises a UV radiation exit window. The UV radiation exit window is configured to transmit at least part of the UV radiation of the light source. At least part of the UV radiation escapes via the radiation exit window to the exterior of the UV-emitting element. Hence, the exit window is transmissive for UV radiation. In general, the window will also be transmissive for visible light. As indicated above, and as will further be explained below, in embodiments the element may be a radiation transmissive plate. In such instance, the window may be a face (or plane) of the element.

The term "radiation transmissive" refers to transmissive for radiation, especially for UV radiation and optionally also for visible radiation.

The UV radiation exit window comprises an upstream window side and a downstream window side. The terms "upstream" and "downstream" relate to an arrangement of items or features relative to the propagation of the light from a light generating means (here the especially the light source), wherein relative to a first position within a beam of light from the light generating means, a second position in the beam of light closer to the light generating means is "upstream", and a third position within the beam of light further away from the light generating means is "downstream". Hence, the upstream window side ("upstream side") is especially directed to the internal of the element and may receive, directly, or after internal reflection, light source light. The downstream window side ("downstream side") may especially be directed to the exterior of the element. This window side may e.g. (temporarily) be in contact with water during use of the system. Note that in plate-like embodiments of the element the upstream window side and a downstream window side may be both sides of the (same) edge (or plane).

The element especially also includes an optical sensor. The sensor is at least partly enclosed by the element, but may in embodiments even be entirely embedded therein. Hence, the optical sensor is configured, like the light source, at the upstream window side of the element. The optical sensor ("sensor") may in embodiments be configured to sense radiation emanating from the downstream window side (into the element). Further, the term "sensor" may also refer to a plurality of sensors, of which optionally two or more may be configured to sense different properties.

The sensor may be configured to sense radiation within the element, which radiation originates from the light source.

In embodiments, the system may be based on the principle of reflection, especially TIR (Total Internal reflection). The light source may be configured to provide the UV radiation (and/or other type of radiation; see below) to the radiation exit window based on the principle of internal reflection. Hence, in embodiments the optical sensor is configured to sense UV radiation (and/or other type of radiation; see below) reflected by said UV radiation exit window. When biofouling is available on the radiation exit window, especially on the downstream window side, more UV radiation (and/or other type of radiation; see below) may escape from the element. Hence, less UV radiation (and/or other type of radiation; see below) may reach the optical sensor. When less UV radiation (and/or other type of radiation; see below) is received by the sensor, the system may—if possible—increase the intensity for anti-biofouling with UV radiation. Hence, even more especially the anti-biofouling system may be configured to increase intensity of said UV radiation when the optical sensor senses a reduction in UV radiation (and/or other type of radiation; see below). The (UV) radiation may be reduced as a result of "frustrated TIR" due to biofouling (at the downstream side of the radiation exit window). The biofouling extracts light from the light exit window. Hence, in embodiments the (sensed) radiation originates from the light source.

The element may in embodiments at least comprise a light source for UV radiation. This UV radiation is used for anti-biofouling. Hence, the UV radiation is used as anti-biofouling radiation. This radiation can also be the basis for the sensor, as the sensor may be configured to sense one or more of reflected UV radiation, scattered UV radiation, and luminescence (from species adjacent to or attached to the radiation exit window).

Hence, in embodiments when using LEDs, the same LED wavelength is used for monitoring and anti-fouling. Hence, the source of the sensor system may in embodiments be a UV LED that is also used for anti-biofouling.

However, alternatively or additionally, a separate light source, herein also indicated as second light source, configured for generating second light source radiation ("second radiation"), can be the basis for the sensor. In such embodiments, the sensor may be configured to sense one or more of reflected second radiation, scattered second radiation, and luminescence (from species adjacent to or attached to the radiation exit window) due to excitation with second radiation.

Hence, the source of the sensor system may be a UV LED (or laser) not substantially used for anti-biofouling. The source of the sensor system may also be a visible LED (or laser). Alternatively or additionally, the source of the sensor system may be an infrared LED (or laser). Hence, in the embodiments above it is referred to UV radiation and/or other type of radiation.

Especially, the sensor is configured to sense reflection of radiation of the light source, especially reflection at the light exit window.

Herein, the term "light" in light source and similar terms may thus also refer to UV radiation and/or IR radiation (and of course visible light). This will be clear from the context. Hence, in embodiments UV light sources may be used. In other embodiments, one or more UV light sources and one or more light sources for one or more of visible and IR may be applied.

As indicated above, the sensor is configured to provide a corresponding optical sensor signal. Hence, the sensor signal is especially related to the radiation that is sensed by the sensor and for which the sensor is configured. For instance, an increase in reflected (UV) radiation may e.g. relate to a larger sensor signal.

Especially, the anti-biofouling system is further configured to provide said UV radiation (for anti-biofouling) in dependence of said optical sensor signal. Hence, when based on the sensor signal the system decides that there is biofouling, or (the amount of) biofouling is increasing, anti-biofouling light may be provided and/or increased (by the system). Alternatively or additionally, also the spectral distribution of the anti-biofouling light may be changed in dependence of the sensor signal (see also below).

The control loop described herein may include or imply a control system, which may be integrated in the element, or which may be configured external from the element. In the latter embodiment, this implies a wired or wireless communication between the element and the control system. Hence, especially the object, or the anti-biofouling system, may further comprise a control system. Hence, the object may comprise such control system. In embodiments the anti-biofouling system comprises the control system, but external from the object. Therefore, in embodiments the anti-biofouling system may further comprise a control system, optionally enclosed by the UV-emitting element. When the control system comprises more than one element, one or more elements may be comprised by the object and/or one or more elements may be configured external from the object.

In an embodiment, the control system comprises a plurality of control systems. For instance, the vessel may comprise a control system, as master control system, with each anti-biofouling system comprising a slave control system. Optionally, the control system may be configured external form the object, i.e. remote from the object. In specific embodiments, a master control system, remote from the object, controls the slave control system comprised by the object, (such as the anti-biofouling system). Hence, for instance the (master) control system may be far away; or not on the vessel, but ashore, such as in a control room of a shipping company. Such master control system may be configured to control anti-biofouling systems of a plurality of objects.

The optical sensor may be sensitive to one or more of UV radiation, visible radiation and IR radiation. Such sensitivity may refer to a subrange of wavelengths within one (or more) of these, for instance an optical sensor substantially only sensitive in the wavelength range of 200-300 nm. The optical sensor may be configured to sense the radiation used Here below, some further embodiments are discussed in more detail.

As indicated above, the UV radiation used for anti-fouling may also be used for sensing the extent of bio-fouling on the radiation exit window. Hence, in embodiments the anti-biofouling system is further configured to control the intensity of said UV radiation in dependence of said optical sensor signal.

As indicated above, not only the UV radiation may be used as basis for the sensor, alternatively or additionally other type of radiation may be applied. This radiation may be provided by the same light source that provides the UV radiation or by a separate light source (second light source). Hence, in embodiments (i) the light source is configured to provide UV radiation and one or more of visible and infrared radiation, and/or (ii) the UV-emitting element comprises a second light source configured to generate one or more of visible and infrared radiation, and wherein the optical sensor is configured to sense one or more of visible and infrared radiation and provide said corresponding sensor signal. Especially, in embodiments the anti-biofouling system is further configured to control one or more of the spectral distribution and the intensity of said UV radiation (and/or one or more of visible and infrared radiation) in dependence of a spectral distribution of the received radiation. This sensor may measure scattered and/or reflected visible and/or IR radiation. As indicated herein, there may be a (physical) blockade between the sensor and light source, to prevent the sensor receiving direct light source light from this light source.

Therefore, in embodiments the optical sensor is configured to sense said UV radiation. Alternatively or additionally, in embodiments the optical sensor is configured to sense one or more of visible and infrared radiation.

Especially, the system comprises a plurality of UV light sources. Even more especially, these may essentially be arranged in a regular pattern. Likewise, the system may include a plurality of sensors (which may essentially be arranged in a regular pattern). In general, an element may include more light sources than sensors, such as a plurality of light sources, but a single sensor, though optionally the element may also include a plurality of sensors. The distances between light sources may be smaller than the distances between the sensors.

Especially, the system may include a plurality of subsets, with each subset a plurality of light sources and one or more sensors. Hence, in embodiments the anti-biofouling system comprises a plurality of light sources, wherein neighboring light sources have mutual light source distances (d1) selected from the range of 0.5-200 mm, such as 2-100 mm, wherein the anti-biofouling system further comprises a plurality of optical sensors, wherein neighboring optical sensors have mutual optical sensor distances (d2) selected from the range of at least 0.5 mm, such as at least 2 mm, like at least 1 cm, such as at least 4 cm, like in the range of 0.5-200 mm. In specific embodiments, the anti-biofouling system comprises a plurality of subsets of light sources and optical sensors, wherein each subset comprises one or more light sources and one or more optical sensors, wherein each subset is configured to provide said UV radiation of the one or more light sources in the subset in dependence of optical sensor signal of the one or more optical sensors in the subset. In yet further embodiments, the biofouling system comprises a plurality of LEDs, wherein the LEDs are configured to generate said UV radiation, wherein the LEDs comprise LED dies, and wherein the LED dies of neighboring LEDs have mutual light source distances (d1) selected from the range of 0.5-200 mm, wherein the anti-biofouling system further comprises a plurality of optical sensors, wherein neighboring optical sensors have mutual optical sensor distances (d2) selected from the range of at least 0.5 mm, such as at least 2 mm, like at least 1 cm, such as at least 4 cm, like in the range of 0.5-200 mm, wherein the anti-biofouling system comprises a plurality of subsets of light sources and optical sensors, wherein each subset comprises one or more light sources and one or more optical sensors, wherein each subset is configured to provide said UV radiation of the one or more light sources in the subset in dependence of optical sensor signal of the one or more optical sensors in the subset. Especially d2>d1, such as d2/d1>2.

Therefore, in specific embodiments the system may comprise a plurality of UV emitting light sources. however, in other embodiments, the system may comprise one or more UV emitting light sources and one or more light sources that emit in the visible or in the infrared. The latter may in specific embodiments be used for the sensing of the internal reflection and/or for other purposes. However, in yet other specific embodiments, the system comprises a plurality of light sources and one or more light sources are configured such that at least part of the light is internally reflected and can be sensed by the optical sensor.

Hence, in specific embodiments the system comprises a plurality of light sources, wherein one or more light sources are configured to provide visible radiation and wherein one or more other light sources are configured to provide UV radiation.

As already indicated above, the system may also comprise a plurality of light sources, wherein each light source is primarily directed to part of the radiation exit window. In this way, a large waveguide may be applied. In such instance, also a plurality of optical sensors may be applied, which allow a dedicated irradiation of the radiation exit window of the waveguide as well a dedicated control of parts of the exit window whether a higher organism touches the exit window or not. Hence, in yet further specific embodiments the anti-biofouling system may comprise a plurality of light sources and a plurality of optical sensors configured in a plurality of subsets of one or more light sources and one or more optical sensors, wherein the one or more light sources of each subset are configured to radiate radiation via respective parts of the radiation exit window, and wherein the control system is configured to control one or more subsets independent of one or more other subsets.

As indicated above, in a further aspect the invention provides an object that during use is at least partly submerged in water, the object comprising the anti-biofouling system as defined herein, wherein the UV-emitting element is configured to irradiate with UV radiation during an irradiation stage one or more of (i) a part of an external surface of said object and (ii) water adjacent to said part of said external surface. As indicated above, the object may especially be selected from the group consisting of a vessel and an infrastructural object.

Herein, the phrase "object that during use is at least partly submerged in water" especially refers to objects such as vessels and infrastructural objects that have aquatic applications. Hence, during use such object will be in general in contact with the water, like a vessel in the sea, a lake, a canal, a river, or another waterway, etc. The term "vessel" may e.g. refer to e.g. a boat or a ship, etc., such as a sail boat, a tanker, a cruise ship, a yacht, a ferry, a submarine, etc. etc. The term "infrastructural object" may especially refer to aquatic applications that are in general arranged substantially stationary, such as a dam, a sluice, a pontoon, an oilrig, etc. etc. The term "infrastructural object" may also refer pipes (for e.g. pumping up ocean water to e.g. a power plant), and other parts of (hydro-electrical) power plants, such as cooling systems, turbines, etc. The term "infrastructural object" may also refer to an oil rig. The term "infrastructural object" may also refer to a structure for harvesting tidal energy and/or for harvesting wave energy and/or for harvesting ocean current derived energy, etc.

The term "external surface" especially refers to the surface that may be in physical contact with water. In the case of pipes this may apply to one or more of the internal pipe surface and the external pipe surface. Hence, instead of the term "external surface" also the term "fouling surface" may be applied. Further, in such embodiments the term "water line" may also refer to e.g. filling level. Especially, the object is an object configured for aquatic (such as marine) applications, i.e. application in or near to a sea or an ocean. Such objects are during their use at least temporarily, or substantially always, at least partly in contact with the water. The object may be at least partly below the water (line) during use, or may substantially be all of its time below the water (line), such as for submarine applications. The invention may e.g. be applied for aquatic (such as marine) anti-fouling, keeping wetted surfaces clean, for off-shore applications, for (sub) sea applications, for drilling platforms, etc.

Due to this contact with the water, biofouling may occur, with the above indicated disadvantages. Biofouling will occur at the surface of an external surface ("surface) of such object. The surface of an (element of the) object to be protected may comprise steel, but may optionally also comprise another material, such as e.g. selected from the group consisting of wood, polyester, composite, aluminum, rubber, hypalon, PVC, glass fiber, etc. Hence, instead of a steel hull, the hull may also be a PVC hull or a polyester hull, etc. Instead of steel, also another iron material, such as an (other) iron alloys may be used Herein, the term "fouling" or "biofouling" or "biological fouling" are interchangeably used. Above, some examples of fouling are provided. Biofouling may occur on any surface in water, or close to water and being temporarily exposed to water (or another electrically conductive aqueous liquid). On such surface biofouling may occur when the element is in, or near water, such as (just) above the water line (like e.g. due to splashing water, such as for instance due to a bow wave). Between the tropics, biofouling may occur within hours. Even at moderate temperatures, the first (stages of) fouling will occur within hours; as a first (molecular) level of sugars and bacteria.

The anti-biofouling system comprises at least an UV-emitting element. Further, the anti-biofouling system may comprise a control system (see also below), an electrical energy supply, etc.

The term "anti-biofouling system" may also refer to a plurality of such systems, optionally functionally coupled to each other, such as e.g. controlled via a single control system. Further, the anti-biofouling system may comprise a plurality of such UV-emitting elements. Herein, the term "UV-emitting element" may (thus) refer to a plurality of UV-emitting elements. For instance, in an embodiment a plurality of UV-emitting elements may be associated to an external surface of the object, such as a hull, or may be comprised by such surface (see also below), whereas e.g. a control system may be configured somewhere within the object, such as in a control room or wheel house of a vessel.

The surface or area on which fouling may be generated is herein also indicated as fouling surface. It may e.g. be the hull of a ship and/or an emission surface of an optical medium (see also below). To this end, the UV-emitting element provides UV radiation (anti-fouling light) that is applied to prevent formation of biofouling and/or to remove biofouling. This UV radiation (anti-fouling light) especially at least comprises UV radiation (also indicated as "UV light"). Hence, the UV-emitting element is especially configured to provide UV radiation. Thereto, the UV-emitting element comprises a light source. The term "light source" may also relate to a plurality of light sources, such as 2-200 (solid state) LED light sources, though many more light sources may also be applied. Hence, the term LED may also refer to a plurality of LEDs. Especially, the UV-emitting element may comprise a plurality of light sources. Hence, as indicated above, the UV-emitting element comprises one or more (solid state) state light sources. The LEDs may be (OLEDs or) solid state LEDs (or a combination of these LEDs). Especially, the light source comprises solid state LEDs. Hence, especially, the light source comprises a UV LED configured to provide one or more of UV-A and UVC light (see also below). UV-A may be used to impair cell walls, whereas UVC may be used to impair DNA. Hence, the light source is especially configured to provide the UV radiation. Herein, the term "light source" especially refers to a solid state light source. The light source(s) may also include (a) solid state laser(s).

Especially, the sensor is radiationally coupled with a light source (or a plurality of light sources). The term "radiationally coupled" especially means that the light source and the sensor are associated with each other so that at least part of the radiation emitted by the light source may be received by sensor via internal reflection (at the radiation exit window).

Especially, the light source or the light sources is (are) LEDs. Hence, in embodiments the anti-biofouling system comprises a plurality of light sources, wherein the light sources comprise LEDs. Alternatively or additionally, the light sources comprise solid state lasers.

Ultraviolet (UV) is that part of electromagnetic light bounded by the lower wavelength extreme of the visible spectrum and the X-ray radiation band. The spectral range of UV light is, by definition between about 100 and 400 nm (1 nm=$10^{-9}$ m) and is invisible to human eyes. Using the CIE classification the UV spectrum is subdivided into three bands: UVA (long-wave) from 315 to 400 nm; UVB (medium-wave) from 280 to 315 nm; and UVC (short-wave) from 100 to 280 nm. In reality many photobiologists often speak of skin effects resulting from UV exposure as the weighted effect of wavelength above and below 320 nm, hence offering an alternative definition.

A strong germicidal effect is provided by the light in the short-wave UVC band. In addition erythema (reddening of the skin) and conjunctivitis (inflammation of the mucous membranes of the eye) can also be caused by this form of light. Because of this, when germicidal UV-light lamps are used, it is important to design systems to exclude UVC leakage and so avoid these effects. In case of immersed light sources, absorption of UV light by water may be strong enough that UVC leaking is no problem for humans above the liquid surface. Hence, in an embodiment the UV radiation (anti-fouling light) comprises UVC light. In yet another embodiment, the UV radiation comprises radiation selected from a wavelength range of 100-300 nm, especially 200-300 nm, such as 230-300 nm. Hence, the UV radiation may especially be selected from UVC and other UV radiation up to a wavelength of about 300 nm. Good results are obtained with wavelengths within the range of 100-300 nm, such as 200-300 nm.

As indicated above, in embodiments the UV-emitting element may be configured to irradiate with said UV radiation (during an irradiation stage) one or more of (i) said part of said external surface and (ii) water adjacent to said part of said external surface. The term "part" refers to part of the external surface of an object, such as e.g. a hull or a sluice (door). However the term "part" may also refer to substantially the entire external surface, such as the external surface of the hull or sluice. Especially, the external surface may comprise a plurality of parts, which may be irradiated with the UV light of one or more light sources, or which may be irradiated with the UV radiation of one or more UV-emitting elements. Each UV-emitting element may irradiate one or more parts. Further, there may optionally be parts that receive UV radiation of two or more UV-emitting elements.

In general, especially when referring to aquatic (such as marine) applications, there may be distinguished between two main embodiments. One of the embodiments includes the part of the external surface being irradiated with the UV radiation with between the light source and UV-emitting element water (or air when above the water line), such as sea water, at least during the irradiation stage. In such embodiment, the part is especially comprised by the "original" external surface of the object. However, in yet another embodiment, the "original" external surface may be extended with a module, especially a relatively flat module, that is attached to the "original" external surface of the object (such as the hull of a vessel), whereby the module itself forms in fact the external surface. For instance, such module may be associated to the hull of a vessel, whereby the module forms (at least part of) the external surface. In both embodiments the UV-emitting element especially comprises a radiating exit surface (see further also below). However, especially in the latter embodiment wherein the UV-emitting element may provide part of said external surface, such radiation exit window may provide the part (as the first part and the radiation exit window may essentially coincide; especially may be the same surface).

Hence, in an embodiment the UV-emitting element is attached to said external surface. In yet a further specific embodiment the radiation exit window of the anti-biofouling system is configured as part of said external surface. Hence, in some of the embodiments the object may comprise a vessel comprising a hull, and the UV-emitting element is attached to said hull. The term "radiation exit window" may also refer to a plurality of radiation exit windows (see also below).

In both general embodiments, the UV-emitting element is configured to irradiate with said UV radiation (during an irradiation stage) water adjacent to said part of said external surface. In the embodiments wherein the module itself forms in fact the external surface, the UV-emitting element is at least configured to irradiate with said UV radiation (during an irradiation stage) said part of said external surface, as it is in fact part of said external surface, and optionally also water adjacent to said part of said external surface. Hereby, biofouling may be prevented and/or reduced.

In an embodiment, a significant amount of a protected surface to be kept clean from fouling, preferably the entire protected surface, e.g. the hull of a ship, may be covered with a layer that emits germicidal light ("anti-fouling light"), in particular UV light.

In yet another embodiment, the UV radiation (anti-fouling light) may be provided to the surface to be protected via a waveguide, such as a fiber.

Hence, in an embodiment the anti-fouling lighting system may comprise an optical medium, wherein the optical medium comprises a waveguide, such as an optical fiber, configured to provide said UV radiation (anti-fouling light) to the fouling surface. The surface of e.g. the waveguide from which the UV radiation (anti-fouling light) escapes is herein also indicated as emission surface. In general, this part of the waveguide may at least temporarily be submerged. Due to the UV radiation (anti-fouling light) escaping from the emission surface, an element of the object that is during use at least temporarily exposed to the liquid (such as seawater), may be irradiated, and thereby anti-fouled. However, the emission surface per se may also be anti-fouled. This effect is used in some of the embodiments of the UV-emitting element comprising an optical medium described below.

Embodiments with optical media are also described in WO2014188347. The embodiments in WO2014188347 are herein also incorporated by reference as they are combinable with the control unit and/or water switch, and other embodiments, described herein.

As indicated above, the invention may also be applied for other applications than aquatic (such as marine) applications, like for (door) knobs, etc.

As indicated above, the UV-emitting element may especially comprise a UV radiation exit window. Hence, in a specific embodiment the UV-emitting element comprises a UV radiation exit window, with the UV-emitting element especially being configured to provide said UV radiation downstream from said UV radiation exit window of said UV-emitting element. Such UV radiation exit window may be an optical window through which the radiation escapes from the UV-emitting element. Alternatively or additionally, the UV radiation exit window may be the surface of a waveguide. Hence, UV radiation may be coupled in the UV-emitting element into the waveguide, and escape from the element via a (part of a) face of the waveguide. As also indicated above, in embodiments the radiation exit window may optionally be configured as part of the external surface of the object. Another term for "escape" can be "outcoupling".

Especially, the (solid state) light source is at least controllable between a first UV radiation level and a second UV radiation level, wherein the first UV radiation level is larger than the second UV radiation level (and wherein the second UV radiation level is smaller than the first radiation level or may even be zero). Hence, in an embodiment the light source can be switched off and can be switched on (during a radiation stage). Further, optionally also the intensity of the UV radiation may be controlled between these two stages, such as a stepwise or continuous UV radiation intensity control. Hence, the light source is especially controllable (and thus its UV radiation intensity is).

In (aquatic (such as marine)) embodiments, the antibiofouling system is especially configured to provide UV radiation to the part of the object or to water adjacent to this part. This especially implies that during an irradiation stage the UV radiation is applied. Hence, there may optionally also be periods wherein no UV radiation is applied at al. This may (thus) not only be due to e.g. a control system switching of one or more of the UV-emitting elements, but may e.g. also be due to predefined settings such as day and night or water temperature, etc. For instance, in an embodiment the UV radiation is applied in a pulsed way.

Hence, in a specific embodiment or aspect, the anti-biofouling system is configured for preventing or reducing biofouling on a fouling surface of an object that during use is at least temporarily exposed to water, by providing an anti-fouling light (i.e. UV radiation) to said fouling surface or water adjacent thereto. Especially, the anti-biofouling system may be configured to provide said anti-fouling light via an optical medium to said fouling surface, wherein the UV-emitting element further comprises (ii) said optical medium configured to receive at least part of the UV radiation (anti-fouling light), the optical medium comprising an emission surface configured to provide at least part of said UV radiation (anti-fouling light). Further, especially the optical medium comprises one or more of a waveguide and an optical fiber, and wherein the UV radiation (anti-fouling light) especially comprises one or more of UVB and UVC light. These waveguides and optical media are herein further not discussed in detail.

The optical medium may also be provided as a (silicone) foil for applying to the protected surface, the foil comprising at least one light source for generating anti-fouling light and a sheet-like optical medium for distributing the UV radiation across the foil. In embodiments the foil has a thickness in an order of magnitude of a couple of millimeters to a few centimeters, such as 0.1-5 cm, like 0.2-2 cm. In embodiments, the foil is not substantially limited in any direction perpendicular to the thickness direction so as to provide substantially large foil having sizes in the order of magnitude of tens or hundreds of square meters. The foil may be substantially size-limited in two orthogonal directions perpendicular to the thickness direction of the foil, so as to provide an anti-fouling tile; in another embodiment the foil is substantially size-limited in only one direction perpendicular to a thickness direction of the foil, so as to provide an elongated strip of anti-fouling foil. Hence, the optical medium, and even also the UV-emitting element, may be provided as tile or as strip. The tile or strip may comprise a (silicone) foil.

Therefore, in specific embodiments the waveguide element may comprise one or more of glass, silicone and a light transmissive polymer.

In an embodiment the UV-emitting element comprises a two-dimensional grid of light sources for generating UV radiation and the optical medium is arranged to distribute at least part of the UV radiation from the two-dimensional grid of light sources across the optical medium so as to provide a two-dimensional distribution of UV radiation exiting the light emitting surface of the light module. The two-dimensional grid of light sources may be arranged in a chicken-wire structure, a close-packed structure, a rows/columns structure, or any other suitable regular or irregular structure. The physical distance between neighboring light sources in the grid may be fixed across the grid or may vary, for example as a function of light output power required to provide the anti-fouling effect or as function of the location of the UV-emitting element on the protected surface/surface to be kept clean (e.g. location on the hull of a ship). Advantages of providing a two-dimensional grid of light sources include that the UV radiation may be generated close to the areas to be protected with UV radiation illumination, and that it reduces losses in the optical medium or light guide and that it is increasing homogeneity of the light distribution. Preferably, the UV radiation is generally homogeneously distributed across the emission surface; this reduces or even prevents under-illuminated areas, where fouling may otherwise take place, while at the same time reducing or preventing energy waste by over-illumination of other areas with more light than needed for anti-fouling. In an embodiment, the grid is comprised in the optical medium. In yet another embodiment, the grid may be comprised by a (silicone) foil.

Further, in an embodiment the optical medium may be disposed proximate (including optionally attached to) to the protected surface and coupled to receive the ultraviolet light, wherein the optical medium has a thickness direction perpendicular to the protected surface, wherein two orthogonal directions of the optical medium orthogonal to the thickness direction are parallel to the protected surface, wherein the optical medium is configured to provide a propagation path of the ultraviolet light such that the ultraviolet light travels within the optical medium in at least one of the two orthogonal directions orthogonal to the thickness direction, and such that, at points along a surface of the optical medium, respective portions of the ultraviolet light escape the optical medium.

In a further aspect, the invention also provides a method of anti-(bio)fouling (a part of) an external surface of an object. Such object includes the waveguide element, which may be in the form of a plate, like an operation table or a cutting board for a kitchen, but also have another shape, such as the knob of a door, or a toilet knob for operating the toilet (flushing the toilet), or a knob of a tap, etc. Also a seating of a toilet may comprise the waveguide element, etcetera. The invention may also be used to reduce biofouling on (parts of) the walls of operating rooms. Therefore, in further aspects or embodiments the invention also provides an object comprising the system as defined herein, wherein the object comprises an external surface, and wherein the radiation exit window is configured as at least part of the external surface, wherein the object is selected from the group comprising a table, an operating table, a cleanroom wall, an operation room wall, and a kitchen wall.

Therefore, in embodiments a table, an operating table, a cleanroom wall, an operation room wall, or a kitchen wall may comprise the herein described waveguide element.

The light source may be configured external from such object and the radiation may be provided into the waveguide element e.g. via an optical fiber. In yet other embodiments, the light source is embedded in the waveguide element.

Herein, the term "object" may in specific embodiments also refer to an arrangement of (different) objects, which especially are functionally connected.

In yet a further aspect, the invention also provides a method for controlling escape of radiation from a waveguide element to the exterior of the waveguide element, radiation, wherein the radiation at least comprises UV radiation, the method comprising sensing internal reflection intensity (I) of within the waveguide element internally reflected radiation, and reducing the intensity of the radiation (of a light source providing the radiation at least comprising UV radiation) as function of reaching a predetermined first threshold of a reduction of the internal reflection intensity (I) over time.

In specific embodiments, the object may be an object that is during use at least temporarily exposed to water, the method comprising: providing the anti-biofouling system as defined herein to the object, generating the UV radiation (during use of the object), optionally as function of one or more of (i) a feedback signal, and (ii) a timer for (periodically) varying the intensity of the UV radiation (anti-fouling light), and providing said UV radiation (during an irradiation stage) to (the part of) the external surface. Such feedback signal may be provided by the sensor. The method may thus further include reducing the intensity of the radiation as function of reaching a predetermined first threshold of a reduction of the internal reflection intensity (I) over time, as well as further activities as defined in relation to the system.

In yet a further aspect, the invention also provides a method of providing an anti-biofouling system to an object, the method comprising providing the anti-biofouling system with the waveguide element to the object. Especially, the object may be configured to be at least temporarily exposed to harmful micro-organisms, such as bacteria, during use of the object. Hence, in embodiments the waveguide element may be attached to the object, to provide the objection comprising the waveguide element.

In embodiments, the invention also provides a method of providing an anti-biofouling system to an object, that during use is at least temporarily exposed to water, the method comprising providing, such as integrating in the object and/or attaching to an external surface, the anti-biofouling system to the object, such as a vessel, with the waveguide element configured to provide said UV radiation to one or more of a part of an external surface of the object and water (being) adjacent to said part (during use), as further defined in the accompanying claims. Especially, the waveguide element is attached to the external surface, or may even be configured as (first) part of the external surface.

The terms "visible", "visible light" or "visible emission" refer to light having a wavelength in the range of about 380-780 nm.

In further embodiments, fouling levels on various areas of the anti-fouling surface can be detected and controlled separately.

In yet further embodiments, the monitoring takes place real-time and the fouling signal from the sensor is used to control the UV radiation of the anti-fouling system. Hence, anti-biofouling radiation especially includes UV radiation. Radiation used for detection with the sensor (reflection, scattering, luminescence) may be one or more of UV, visible and IR radiation, i.e. especially substantially any radiation between about 200 and 1500 nm.

Especially, any action described herein may be executed with a man-made device. For instance, a term "sensing" may refer to sensing with a sensor, or a term like "determining" may refer to determining with a processor.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIGS. 1a-1h schematically depict some general aspects;

Figure 1E:
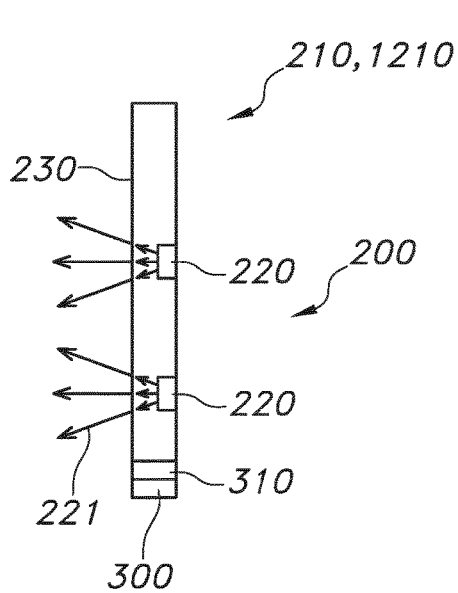

The drawings are not necessarily to scale.

DETAILED DESCRIPTION OF THE EMBODIMENTS

FIG. 1a schematically depicts an embodiment of an anti-biofouling system 200 which comprises an UV-emitting element 210. The UV-emitting element 210 comprises a UV radiation exit window 230. The UV-emitting element 210 at least partly encloses a light source 220 configured to provide UV radiation 221. Here, by way of example three light sources 220 are depicted. Here, the UV-emitting element 210 is configured as waveguide, with elements embedded therein. Hence, the light sources 220 are embedded in the waveguide. The UV radiation exit window 230 is configured to transmit at least part of the UV radiation 221 of the light source 220. The UV radiation exit window 230 comprises an upstream window side 231, here directed to the light source(s) and a downstream window side 232. The UV-emitting element 210 also at least partly encloses an optical sensor 310 configured to sense radiation 421 emanating from the downstream window side 232. Here, the sensor 310 is also embedded in the waveguide. The sensor 310 is configured to provide a corresponding optical sensor signal, corresponding to the radiation 421 emanating from the downstream side. Further, the anti-biofouling system 200 is further configured to provide said UV radiation 221 in dependence of said optical sensor signal. Radiation 421 may include one or more of scattering of light source radiation 221 (by biofouling at the downstream window side 232), reflection of light source radiation 221 (at the upstream window side 231), and luminescence of biofouling (at the downstream window side 232), indicated with reference 5.

Especially, radiation 421 includes reflection of light source radiation 221 (unless all radiation would be coupled out).

Here, in this schematically depicted embodiment the same type of light source is used for anti-biofouling radiation 221 and for the control loop with the sensor 310; however, this is not necessarily the case. Reference 305 refers to electronics or a control element (see also below) for controlling the radiation 221 of the light sources 220 as function of the optical sensor 310. Here, controlling may refer to one or more of controlling the intensity and controlling the spectral distribution. The combination of sensor 310 and light source that generates radiation that is used directly or indirectly, such as by reflection, scattering, luminescence, is herein also indicated as sensor system. The light source is herein also indicated as source of the sensor system.

The term "controlling" especially refers to determining the behavior or supervising the running of the light source, especially thus one or more of the intensity and the spectral distribution, especially at least the intensity.

Note that in the embodiment schematically depicted in FIG. 1b and also other embodiments described herein and/or depicted herein include a radiation emitting element, especially here thus the UV emitting element 220, which encloses at least partly, or even substantially entirely, the light source and the sensor.

FIGS. 1b-1d schematically depict embodiments of an object 10 that during use is at least partly submerged in water 2, see the water line 13. The object 10, such as a vessel or a sluice, see also below, further comprises an anti-biofouling system 200 comprising an UV-emitting element 210, especially for application of UV radiation 221 to a part 111 of an external surface 11 of the object 10, such as a hull or part or a hull. Here, two embodiments are shown wherein the anti-biofouling system 200, or more especially the UV-emitting element 210 is part of an outer surface, and thereby forms in fact part of the outer surface (FIG. 1a) or wherein the UV-emitting element 210 is configured to irradiate the outer surface and does not necessarily form part of an outer surface, such as a hull of a ship (FIG. 1c). For instance, the object 10 is selected from the group consisting of a vessel 1 and an infrastructural object 15 (see also below).

The UV-emitting element 210 comprises one or more light sources 220 and may thus especially be configured to irradiate with said UV radiation 221 during an irradiation stage one or more of (i) said part 111 of said external surface 11 and (ii) water adjacent to said part 111 of said external surface 11. The former variant applies especially the embodiment of FIG. 1c, and the latter embodiment especially applies to both embodiments of FIGS. 1b-1c. Note however that when an external surface of the UV-emitting element 210 is configured as external surface of the object 10, of course the part 111 is irradiated per se with the UV radiation 21.

Hence, the UV-emitting element 210 comprises a UV radiation exit window 230 and the UV-emitting element 210 is configured to provide said UV radiation 221 downstream from said UV radiation exit window 230 of said UV-emitting element 210.

Especially, the light source 220 is at least controllable between a first UV radiation level and a second UV radiation level, wherein the first UV radiation level is larger than the second UV radiation level (and wherein the second UV radiation level is smaller than the first radiation level (including e.g. zero).

As indicated above, the term "vessel", indicated with reference 1, may e.g. refer to e.g. a boat or a ship (ref 10a in FIG. 1d), etc., such as a sail boat, a tanker, a cruise ship, a yacht, a ferry, a submarine (ref. 10d in FIG. 1d), etc. etc., like schematically indicated in FIG. 1d. The term "infrastructural object", indicated with reference 15, may especially refer to aquatic applications that are in general arranged substantially stationary, such as a dam/sluice (references 10e/10f in FIG. 1d), a pontoon (ref. 10c in FIG. 1d), an oilrig (ref. 10b in FIG. 1d), etc. etc.

FIG. 1e schematically depicts in more detail an embodiment of the anti-biofouling system 200, here by way of example including an integrated control system 300 and an integrated sensor 310.

Figure 1F:
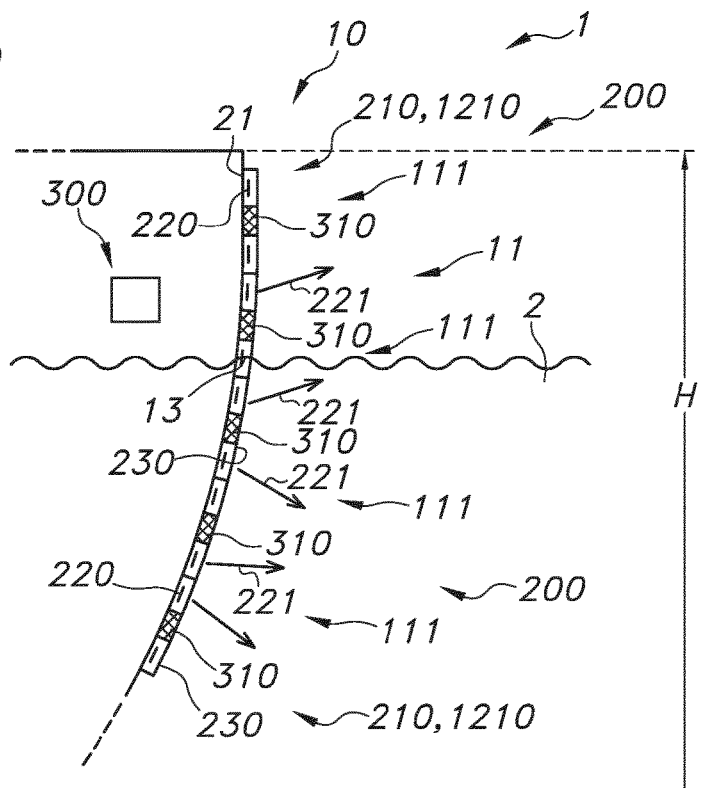

FIG. 1f schematically depicts an external surface 11 of an object 10, such as a vessel wall or a wall of an infrastructural object, with by way of example a plurality UV-emitting elements 210 (here associated to a hull 21 of a vessel 1). Alternatively or additionally, a plurality of functionally coupled or independently functioning anti-biofouling systems 200 may be applied.

FIG. 1f also schematically depicts the embodiment wherein the anti-biofouling system 200 comprises a plurality of UV-emitting elements 210 (with a plurality of light sources), a plurality of radiation exit windows 230, and a plurality of said parts 111, wherein the plurality of light sources 220 are configured to provide said UV radiation 221 via said plurality of radiation exit windows 23 to said plurality of parts 111, and wherein said plurality of parts 111 are configured at different heights of the object 10, and wherein the control system 300 is configured to control the light sources 220 individually as function of said input information. For instance, in an embodiment the control system 300 may be configured to control the light sources 220 individually as function of the positions of the parts 111 of the external surface 11 relative to the water.

Figure 1G:
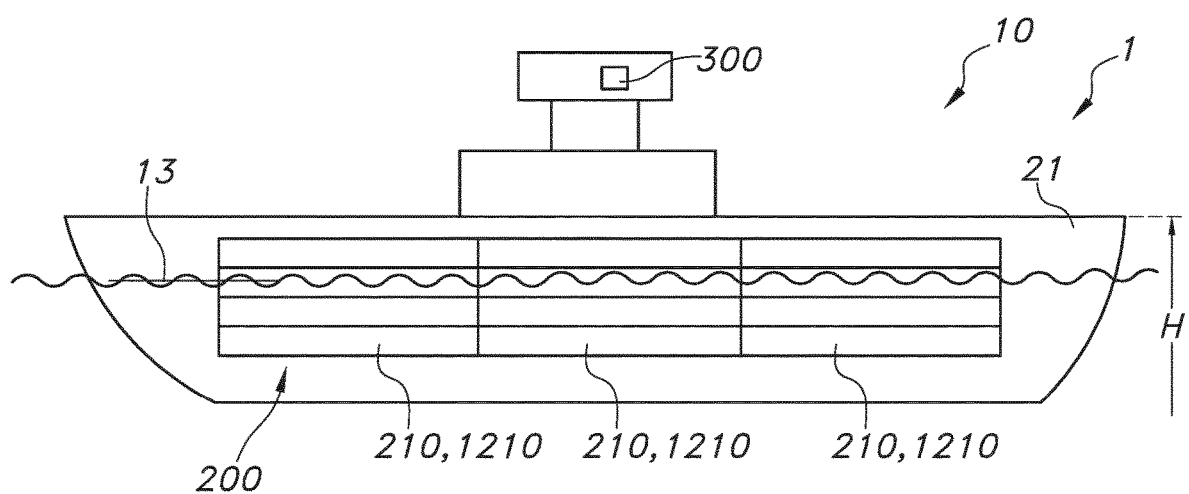

FIG. 1g schematically depicts an embodiment wherein a vessel 1, as embodiment of the object 10, comprises a plurality of anti-biofouling systems 200 and/or a one or more of such anti-biofouling systems 200 comprising a plurality of UV-emitting elements 210. Dependent upon the height of the specific such anti-biofouling system 200 and/or the height of the UV-emitting elements 210, such as relative to a water (line), the respective UV-emitting elements 210 may be switched on.

Figure 1H:
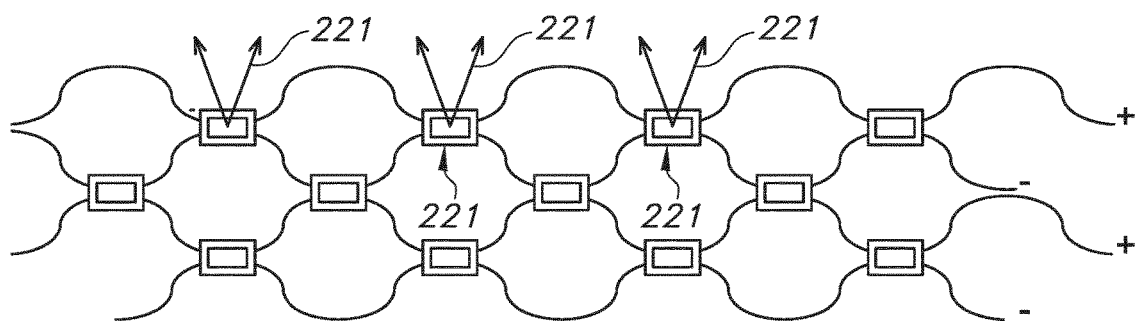

FIG. 1h shows a chicken-wire embodiment where light sources 210, such as UV LEDs, are arranged in a grid and connected in a series of parallel connections. The LEDs can be mounted at the nodes either through soldering, glueing or any other known electrical connection technique for connecting the LEDs to the chicken wires. One or more LEDs can be placed at each node. DC or AC driving can be implemented. If AC is used, then a couple of LEDs in anti-parallel configuration may be used. The person skilled in the art knows that at each node more than one couple of LEDs in anti-parallel configuration can be used. The actual size of the chicken-wire grid and the distance between UV LEDs in the grid can be adjusted by stretching the harmonica structure. The chicken-wire grid may be embedded in an optical medium. Above, especially active prevention applications are described, wherein the anti-biofouling system 200 switches off, or switches specific UV-emitting elements 210 or specific light sources 220 off, dependent upon contact with the water, a signal of a sensor, etc. etc. However, alternatively or additionally, also warning signals or messages may be used to warn a person of danger.

Figure 2A:
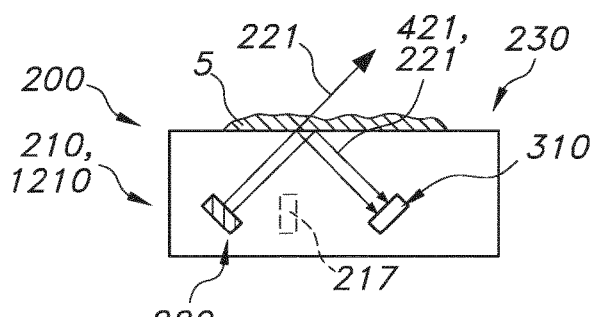
FIGS. 2a-2c schematically depict some embodiments and variants.

FIGS. 2a schematically depicts a variant wherein internal reflection (or total internal reflection TIR) is used as input for the sensor 310, respectively. The internal reflection may decrease with increasing biofouling 5. Here, by way of example the light source 220, which is also used for the generation of UV radiation as anti-biofouling light is applied (in the sensor system); however, also an alternative light source may be applied (see also FIG. 2c). FIG. 2a by way of example also includes a blocking element or physical blockade, indicated with reference 217 which is configured to prevent light source radiation, indicated with reference 221, to directly reach the sensor 310.

As schematically shown in FIG. 2a, the waveguide element 1210 is configured to receive at least part of the radiation 221 and to radiate at least part of the radiation 221 to the exterior of the waveguide element 1210 via the radiation exit window 230. Further, the waveguide element may be configured to internally reflect part of the radiation 221 at the radiation exit window 230. This reflected radiation can be measured by the sensor 310.

Figure 2B:
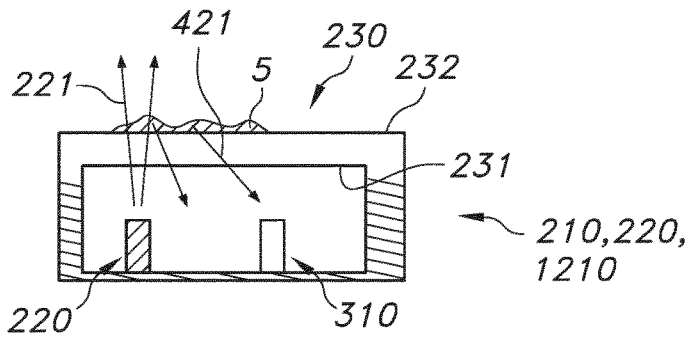

FIG. 2b schematically depicts an embodiment wherein luminescence of biofouling 5 is used. This luminescence may be in the visible and/or infrared. Excitation may be with the light source 220 or an alternative light source (see also FIG. 2c).

Here, by way of example a housing with a separate radiation exit window 230 is schematically depicted, instead of a waveguide plate as used in many of the other schematic drawings. Hence, the UV-emitting element may be a plate-like module, with one or more relevant elements at least partly, or even entirely, embedded therein. However, the UV element may also include a housing enclosing at least partly, or even entirely, one or more relevant elements. The one or more relevant elements at least comprise the light source, which is configured to provide light source radiation, especially the UV radiation.

Figure 2C:
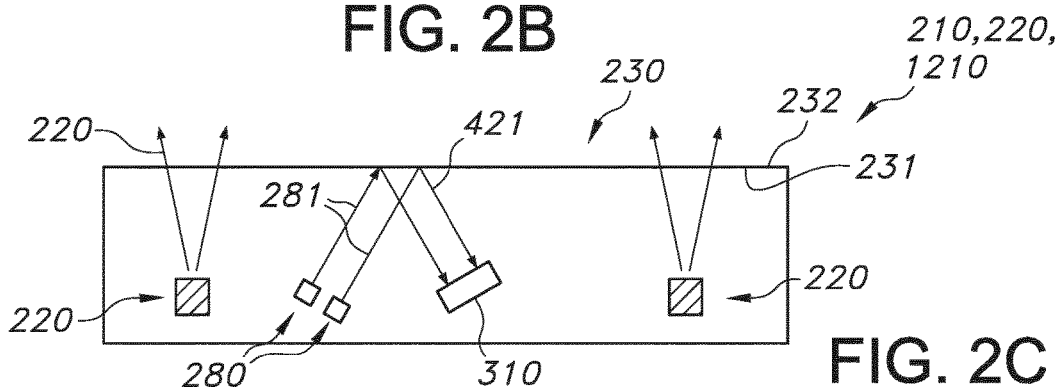

FIG. 2c schematically depicts an embodiment wherein the system 200 comprises a second light source 280 configured to generate one or more of visible and infrared radiation, herein indicated as second light source light 281, and wherein the optical sensor 310 is configured to sense one or more of visible and infrared radiation and provide said corresponding sensor signal. Here, by way of examples two second light sources 280 are applied, e.g. to provide different types of light, like blue and green, or visible and IR, etc. The optical sensor 310 may be configured to sense one or more of visible and infrared radiation and provide said corresponding sensor signal.

Note that when in addition when visible or IR radiation as input for the sensor system is desired, one may also use light sources 220 which are configured to provide UV radiation 221 and one or more of visible and infrared radiation.

Figures 3A, 3B:
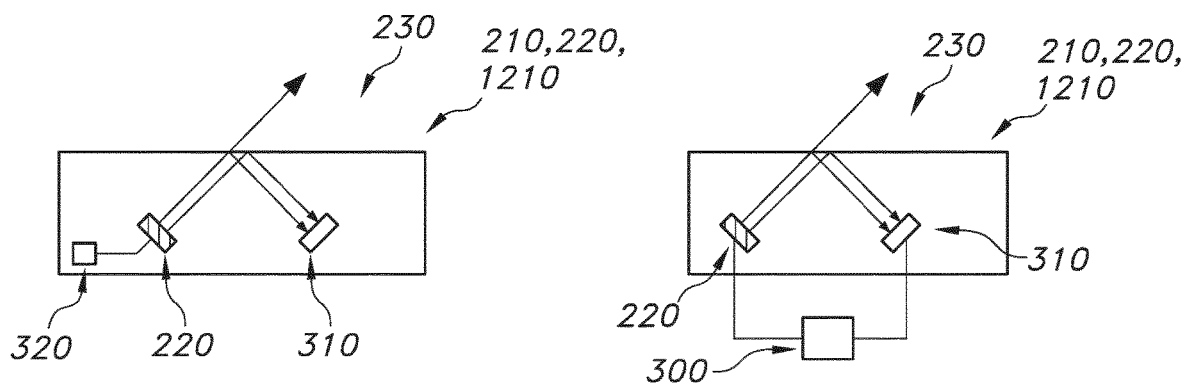
FIGS. 3a-3b schematically depict some further embodiments and variants.

The anti-biofouling system 200 may further including a control element 320 configured to correct the sensor signal for a dependency on the UV radiation intensity of the light source 220. The control element 320 may also be configured to minimize variations in the UV radiation intensity of the light source 220, as schematically depicted in FIG. 3a. In embodiments, the control element 320 may be comprised by the control system 300 (not depicted in this schematical drawing).

Referring to FIGS. 2a-2c and 3a-3b, and other embodiments described herein but not depicted, the light source and the sensor are especially configured at the same side of the radiation exit window 230. Referring to FIGS. 2a-2c and 3a-3b, and other embodiments described herein but not depicted, the light source and the sensor are especially configured at the same side of the upstream window side 231.

It is further noted that (thus) the light source and optical sensor can both be embedded in the light emitting element, even more especially in the waveguide, such as a silicone waveguide.

The waveguide especially comprises a radiation transmissive material, such as glass, quartz, (fused) silica, silicone, fluoropolymer etc.

Figures 4A, 4B:
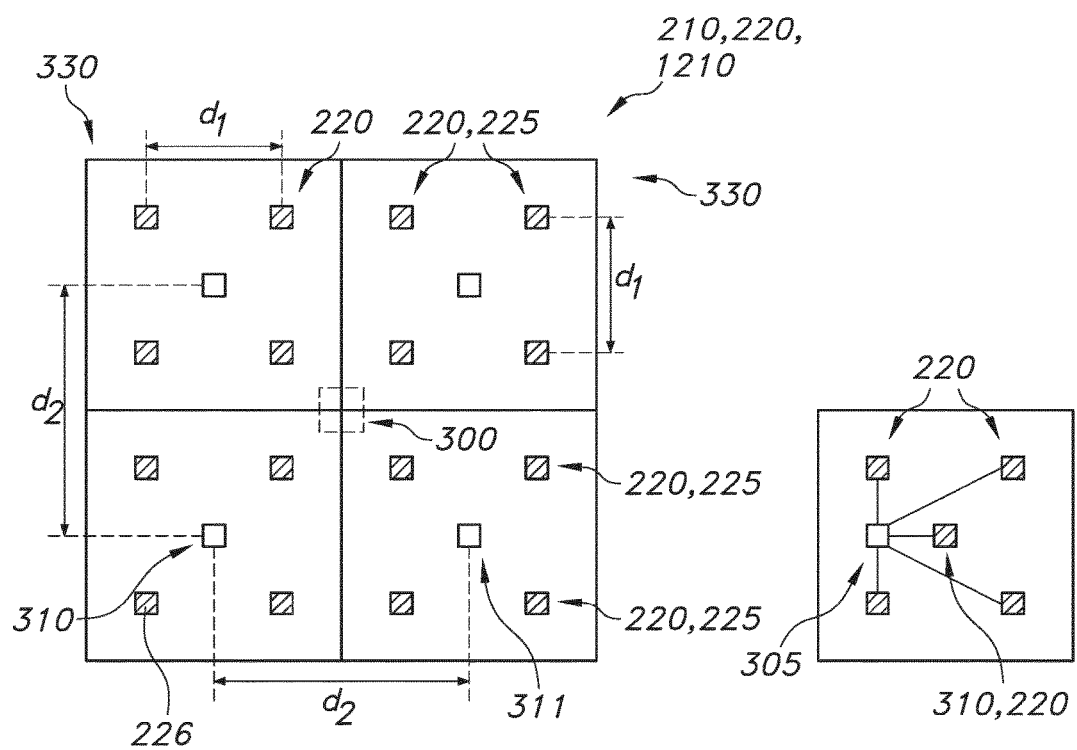
FIGS. 4a-4b schematically depict some further embodiments and variants.

FIG. 4a schematically depicts an embodiment of the anti-biofouling system 200 comprising a plurality of light sources 220. Here, the light sources 220 comprise LEDs 225. The LEDs comprise LED dies 226. The LED dies 226 of neighboring LEDs 225 have mutual light source distances d1, especially selected from the range of 0.5-200 mm. As shown, the anti-biofouling system 200 further comprises a plurality of optical sensors 310. Neighboring optical sensors have mutual optical sensor distances d2, especially selected from the range of at least 4 cm, such as in the range of 10-100 cm. Here, the anti-biofouling system 200 comprises a plurality of subsets 330 of light sources 220 and optical sensors 310, wherein each subset 330 comprises one or more light sources 220 and one or more optical sensors 310. Especially, each subset 330 is configured to provide said UV radiation 221 of the one or more light sources 220 in the subset 330 in dependence of optical sensor signal of the one or more optical sensors 310 in the subset 330. A control system may be included in one or more elements 210 or there may e.g. be a central control system 300, schematically indicated with the dashed square. Note that the control system 300 may also be remote from the elements 210.

FIG. 4b schematically depicts an embodiment wherein a light source 220, i.e. here a solid state light source, is configured as sensor. To this end electronics or a control element 305 may be included to have the solid state light source function as sensor 310. Optionally, this light source may be controlled by the electronics or control element 305 to switch between a sensing stage and a radiation stage.

Electronics or a control element 305 may be comprised by a control system 300 (not depicted here).

Figure 5A:
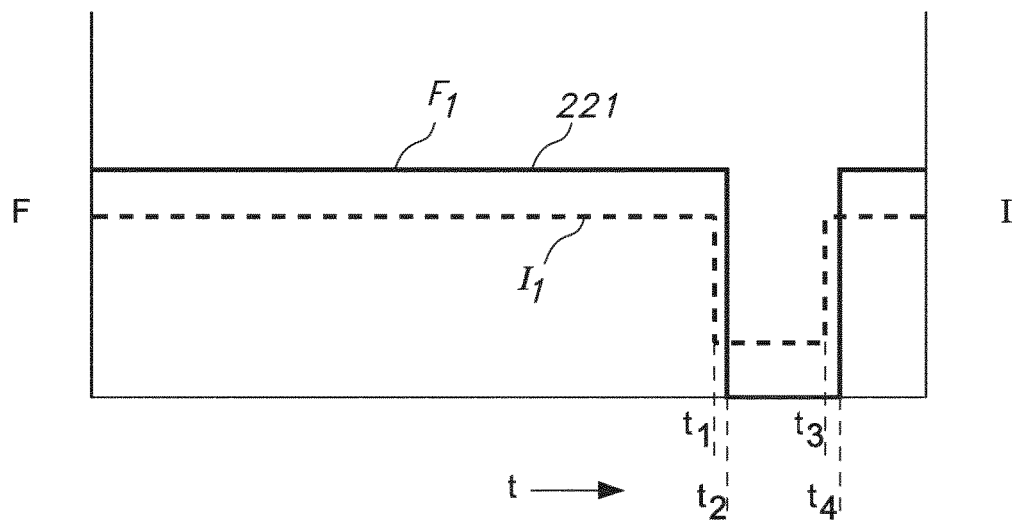
FIGS. 5a-5b schematically show some possible schemes.

FIG. 5a schematically depicts a scheme with on the x-axis the time, on the left y-axis the intensity of the anti-fouling light, with a continue line indicated with $F_1$, and on the right y-axis the sensor signal which senses the reflected light, with a dashed curve indicated the signal, which dashed curve is indicated with reference $I_1$. When an object, such as a human touches for some time the radiation exit window (surface of the waveguide), there will be a sudden drop in the internally reflected light, such as at t1. Shortly thereafter the intensity of the UV radiation is dropped by a control system. Here, the intensity is dropped to zero at t2. When the object removes from the waveguide, here at t3, the internal reflected light increase, as seen with the increase to the essentially original level of $I_1$. Shortly thereafter, at t4, the intensity of the UV radiation is increased to the essentially original level of $F_1$. The difference over time (between t1 and t2, or t3 and t4, respectively) may be very short, as the control system may essentially immediately react (for instance when the control time is kept at a minimum).

Figure 5B:
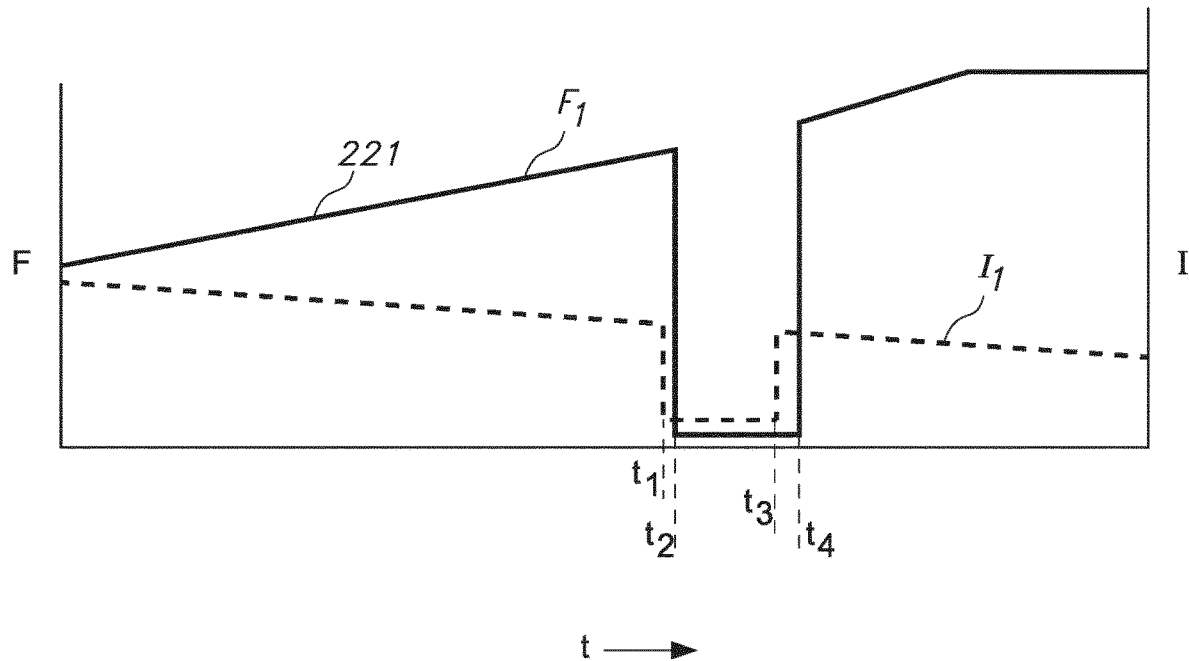

FIG. 5b schematically depicts a similar example, but with some variations. Here, apparently the biofouling increases, as the internal reflection $I_1$ decrease. This increase may be tried to be stopped by also increasing the intensity of the UV radiation $F_1$ (on the time scale shown, this has apparently not yet the desired effect). A contact with a human or other object may have the same result as above. However, in this schematical example by way of example the UV radiation intensity F1 is not dropped to zero. When the object is removed, the UV radiation intensity may be increased to a level that may be associated with the then measured internal reflection intensity I1 according to a predefined relation between UV intensity and internal reflection intensity.

As the UV radiation F1 is changed, it is clear that the first and second thresholds were reached in the examples of FIGS. 5a and 5b.

In embodiments, when the first threshold is reach, the system may also provide one or more of an acoustic signal, a light signal, and a vibration signal. This may warn the higher organism touching the radiation exit window. The light signal especially relates to essentially one or more of visible and IR radiation, especially at least visible radiation.

Figure 6A:
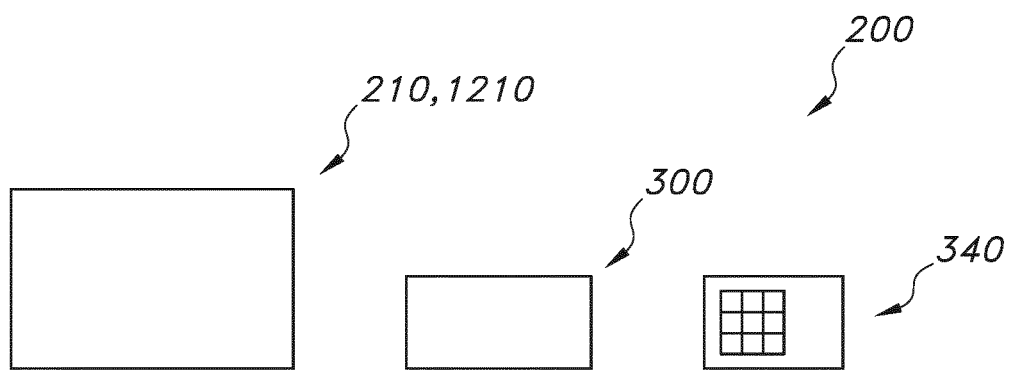
FIGS. 6a-6b schematically depict some further aspects.

FIG. 6a schematically depicts a system also including a user interface 340. The user interface may in embodiments be a graphical user interface. The user interface may especially be external from the waveguide element 1210, though this is not necessarily the case.

Figure 6B:
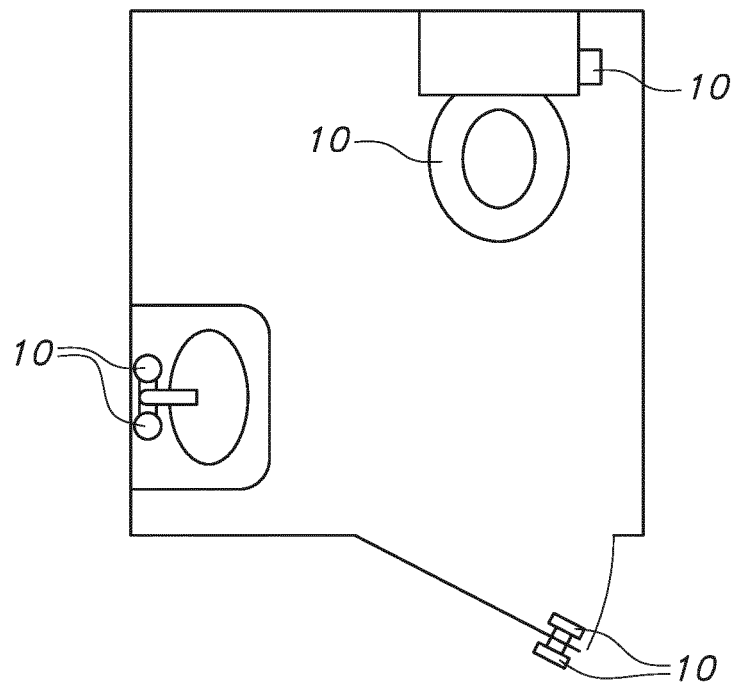

FIG. 6b very schematically shows a bath room with a toilet, including a toilet seat, a sink with a tap with a tap knob, as well as a door with an internal knob and an external knob. Here, by way of example the internal knob, the external knob, the tap knob, and the toilet seat are all objects as defined herein.

In embodiments, the light can be switched on again after a predetermined time; or even better, after a similar but negative step in the outcoupling is observed. This implies that the object touching the surface, has left.

In embodiments, depending on the size of the UV protected surface, multiple sensors could be integrated, together with sectional driving of the UV emission. Thus, one could locally switch off the UV source, in response to a local 'disturbance'.

Any 'active surface' using UV emission for biological "Safety reasons', could benefit from this idea. One could think of doorknobs of public restrooms, cutting boards in a kitchen, hospital equipment or tables used in operation rooms, etc.

The term "substantially" herein, such as in "substantially all light" or in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention further applies to a device comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Furthermore, some of the features can form the basis for one or more divisional applications.

The invention claimed is:

1. A system comprising:
a waveguide element,
wherein the waveguide element comprises a radiation exit window,
wherein the waveguide element is configured to receive radiation,
wherein the radiation comprises UV radiation,
wherein the waveguide element is configured to radiate at least part of the radiation via the radiation exit window,
wherein the waveguide element is configured to reflect part of the radiation at the radiation exit window;
an optical sensor, wherein the optical sensor is configured to sense an internal reflection intensity of the reflected radiation;
a control system,
wherein the control system is coupled to the optical sensor,
wherein the control system is configured to reduce the intensity of the radiation as function of reaching a predetermined first threshold of a reduction of the internal reflection intensity over time.

2. The system according to claim 1,
wherein the control system is configured to reduce the intensity of the radiation only when in a predetermined control period a predetermined second threshold of an increase of the internal reflection intensity over time does not occur,
wherein the predetermined first threshold of a reduction of the internal reflection intensity over time is a reduction of the internal reflection intensity sensed by the optical sensor of at least 1% in at maximum 1 seconds.

3. The system according to claim 2,
wherein the predetermined second threshold is selected from the range of $0.1\%/s \leq |\Delta I/\Delta t| \leq 100\%/s$,
wherein $\Delta I$ is the increase in internal reflection intensity in percent,
wherein $\Delta I > 0\%$, wherein $\Delta t$ is the time period in which such increase $\Delta I$ occurs,
wherein $\Delta t$ is at maximum 1 second.

4. The system according to claim 3,
wherein the control system is configured to reduce the radiation as function of reaching the predetermined first threshold of the reduction of the internal reflection intensity over time to a first intensity level of the radiation larger than 0 W, wherein the control system is configured to increase the radiation as function of the predetermined second threshold of the increase over time of the internal reflection intensity to a predetermined second intensity level of the radiation, wherein the predetermined second intensity level of the radiation is in the range of +/−10% of the intensity level of the radiation before the reduction to the first intensity level of the radiation.

5. The system according to claim 4, wherein the system is configured to radiate at least part of the radiation to an exterior of the waveguide element according to a predetermined relation between intensity of the radiation and the internal reflection intensity, wherein the internal reflection intensity is sensed by the optical sensor, and wherein the predetermined second intensity level of the radiation is the intensity level of the radiation associated with the internal reflection intensity sensed by the optical sensor.

6. The system according to claim 2, further comprising a user interface, wherein the control system further comprises a safety routine, wherein the safety routine is arranged such that after a reduction of the intensity of the radiation due to reaching the predetermined first threshold of the internal reflection intensity, the intensity of the radiation can only be increased upon an instruction via the user interface.

7. The system according to claim 1, wherein the predetermined first threshold is selected from the range of $0.1\%/s \leq |\Delta I/\Delta t| \leq 400\%/s$, wherein $\Delta I$ is the reduction in internal reflection intensity in percent, wherein $\Delta I < 0\%$, wherein $\Delta t$ is the time period in which such reduction $\Delta I$ occurs, wherein $\Delta t$ is at maximum 1 second.

8. The system according to of claim 7, wherein the control system is configured to increase the intensity of the radiation as function of a predetermined second threshold of an increase of the internal reflection intensity over time.

9. The system according to claim 7, further comprising a user interface, wherein the control system further comprises a safety routine, wherein the safety routine is arranged such that after a reduction of the intensity of the radiation due to reaching the predetermined first threshold of the internal reflection intensity, the intensity of the radiation can only be increased upon an instruction via the user interface.

10. The system according to of claim 1, wherein the control system is configured to increase the intensity of the radiation as function of a predetermined second threshold of an increase of the internal reflection intensity over time.

11. The system according to claim 1, further comprising a user interface, wherein the control system further comprises a safety routine, wherein the safety routine is arranged such that after a reduction of the intensity of the radiation due to reaching the predetermined first threshold of the internal reflection intensity, the intensity of the radiation can only be increased upon an instruction via the user interface.

12. The system according to claim 1, further comprising a light source, wherein the light source is configured to provide the radiation.

13. The system according to claim 1, further comprising:

a plurality of light sources; and a plurality of optical sensors, wherein the plurality of light sources and the plurality of optical sensors are configured in a plurality of subsets, wherein each subset comprises of one or more light sources and one or more optical sensors, wherein the one or more light sources of each subset are configured to radiate radiation via the radiation exit window, wherein the control system is configured to control one or more subsets independent of one or more other subsets.

14. An object comprising the system according to claim 1, wherein the object comprises an external surface, wherein the radiation exit window is configured as at least part of the external surface, wherein the object is selected from the group consisting of a door knob, a tap knob, a toilet knob, a toilet seat, a railing, a kitchen cutting board, and a medical device.

15. An object comprising the system according to claim 1, wherein the object comprises an external surface, wherein the radiation exit window is configured as at least part of the external surface, wherein the object is selected from the group consisting of a table, an operating table, a cleanroom wall, an operation room wall, and a kitchen wall.

16. An object comprising the system according to claim 1, wherein the object is at least partly submerged in water during use, wherein the waveguide element is configured to irradiate with radiation a part of an external surface of the object, wherein the waveguide element is configured to irradiate water adjacent to the part of the external surface, wherein the object is selected from the group consisting of a vessel and an infrastructural object.

17. A method for controlling escape of radiation from a waveguide element comprising:

sensing an internal reflection intensity within the waveguide element; and reducing the intensity of the radiation as function of reaching a predetermined first threshold of a reduction of the internal reflection intensity over time wherein the radiation comprises UV radiation.

* * * * *